(12) United States Patent
Marin et al.

(10) Patent No.: US 12,702,289 B2
(45) Date of Patent: Aug. 11, 2026

(54) SYSTEM FOR DETERMINING A SUBJECTIVE VALUE OF AN OPTICAL FEATURE OF AT LEAST A CORRECTIVE LENS ADAPTED TO AN EYE OF A SUBJECT AND ASSOCIATED METHOD

(71) Applicant: Essilor International, Charenton-le-Pont (FR)

(72) Inventors: Gildas Marin, Charenton-le-Pont (FR); Martha Hernandez-Castaneda, Charenton-le-Pont (FR); Adele Longo, Charenton-le-Pont (FR); Aurelie Le Cain, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 718 days.

(21) Appl. No.: 17/906,712

(22) PCT Filed: Mar. 17, 2021

(86) PCT No.: PCT/EP2021/056837

§ 371 (c)(1),
(2) Date: Sep. 19, 2022

(87) PCT Pub. No.: WO2021/185917

PCT Pub. Date: Sep. 23, 2021

(65) Prior Publication Data

US 2023/0139007 A1 May 4, 2023

(30) Foreign Application Priority Data

Mar. 20, 2020 (EP) .................................... 20305297

(51) Int. Cl.
*A61B 3/00* (2006.01)
*A61B 3/028* (2006.01)

(52) U.S. Cl.
CPC .......... *A61B 3/0025* (2013.01); *A61B 3/0285* (2013.01)

(58) Field of Classification Search
CPC .... A61B 3/0025; A61B 3/0285; G16H 10/20; G16H 50/20; G16H 50/50; G06N 3/08; G06N 5/01
See application file for complete search history.

(56) References Cited

U.S. PATENT DOCUMENTS

2011/0211163 A1 9/2011 Meuse et al.
2012/0075586 A1 3/2012 Kirschen et al.
(Continued)

FOREIGN PATENT DOCUMENTS

EP 2 779 889 A1 4/2013
EP 3 272 274 A1 7/2016
(Continued)

OTHER PUBLICATIONS

Japanese Office Action issued Nov. 5, 2024 in Japanese Patent Application No. 2022-552620 (with English translation), citing documents 1 and 15 therein, 6 pages.
(Continued)

*Primary Examiner* — Jack Dinh
(74) *Attorney, Agent, or Firm* — Oblon, McClelland, Maier & Neustadt, L.L.P.

(57) ABSTRACT

A system for determining a value of a magnitude associated with a subjective value of an optical feature of at least a corrective lens adapted to an eye of a subject, by implementing a subjective test where the subject is asked to describe his visual performance in a plurality of real optical conditions by choosing one descriptive answer among a set of possible descriptive answers. The system includes one or more processor programmed to collect the results of the subjective test, performed by asking the subject to describe
(Continued)

Figure 1:
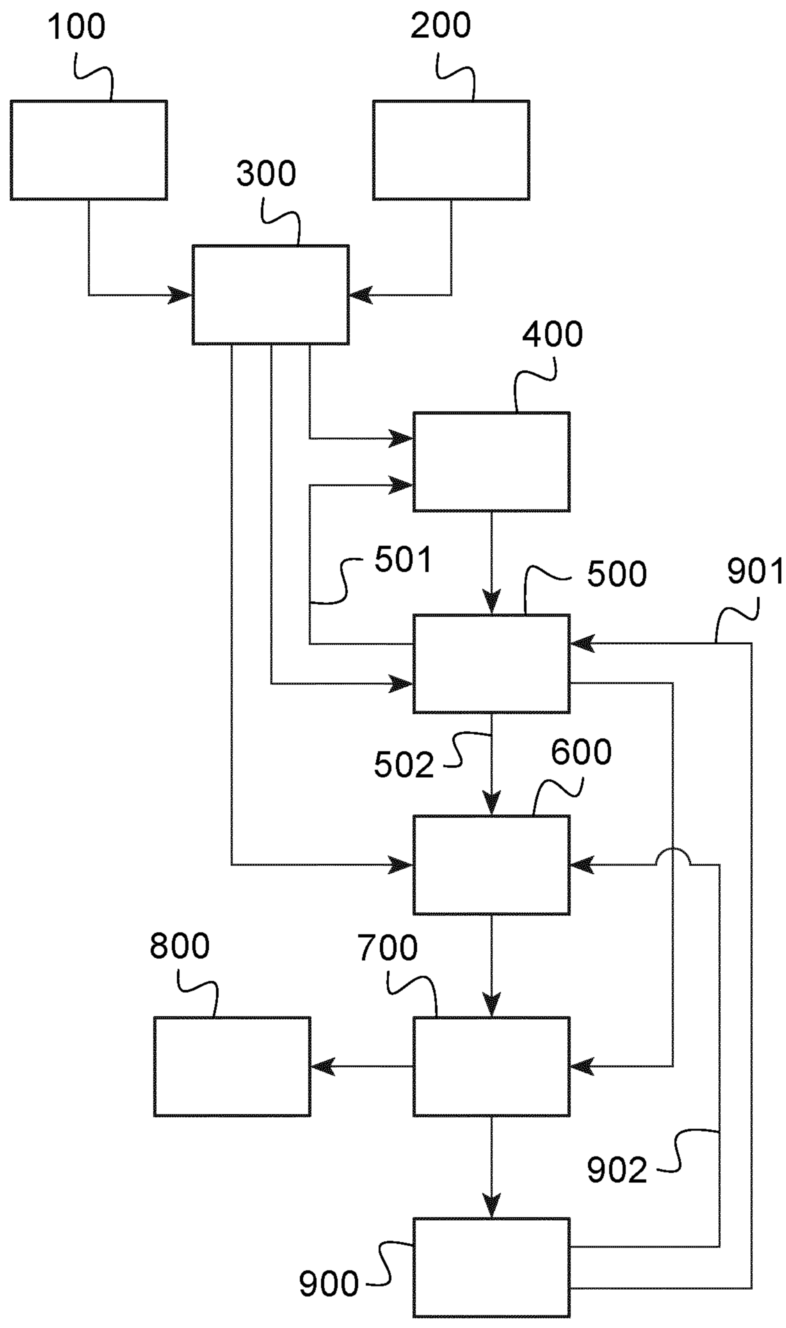

his visual performance in each real optical condition of the plurality of real optical conditions by choosing, for each real optical condition, one descriptive answer, the results comprising each descriptive answer chosen and the corresponding real optical condition, and determine the value of the magnitude by taking into account the initial model and each descriptive answer collected.

18 Claims, 4 Drawing Sheets

(56) References Cited

U.S. PATENT DOCUMENTS

| | | | |
|---|---|---|---|
| 2013/0176534 | A1 | 7/2013 | Frankfort et al. |
| 2013/0335707 | A1 | 12/2013 | Meuse et al. |
| 2015/0150443 | A1 | 6/2015 | Frankfort et al. |
| 2016/0331226 | A1 | 11/2016 | Nauche et al. |
| 2017/0027435 | A1 | 2/2017 | Boutinon et al. |
| 2017/0258316 | A1 | 9/2017 | Benner et al. |
| 2019/0261848 | A1 | 8/2019 | Marin et al. |

FOREIGN PATENT DOCUMENTS

| | | | |
|---|---|---|---|
| EP | 3 321 831 | A1 | 5/2018 |
| EP | 3 598 211 | A1 | 1/2020 |
| FR | 3 050 922 | A1 | 11/2017 |
| JP | 2007-533352 | A | 11/2007 |
| WO | WO 2015/027225 | A1 | 2/2015 |
| WO | WO 2017/021663 | A1 | 2/2017 |
| WO | WO 2018/015381 | A2 | 1/2018 |

OTHER PUBLICATIONS

International Search Report mailed on Jun. 4, 2021 in PCT/EP2021/056837 filed on Mar. 17, 2021 (citing references 3-8 & 20-22 therein, 3 pages).

SYSTEM FOR DETERMINING A SUBJECTIVE VALUE OF AN OPTICAL FEATURE OF AT LEAST A CORRECTIVE LENS ADAPTED TO AN EYE OF A SUBJECT AND ASSOCIATED METHOD

TECHNICAL FIELD OF THE INVENTION

The invention relates to a system and a method for determining a subjective value of an optical feature of at least a corrective lens adapted to an eye of a subject.

BACKGROUND INFORMATION AND PRIOR ART

In order to provide visual equipment adapted to the visual defect of a subject, it is necessary to estimate this visual defect.

A first possibility is to measure objective values of optical features of the eye of the subject.

It is also known to determine subjective values of the optical features of the corrective lens needed by the subject through subjective tests.

In practice, the subject's vision is tested during a subjective test protocol, using a phoropter allowing placing successively in front of his eye lenses with different values of said optical feature.

This test protocol may be achieved using a classical phoropter or a phoropter having two complex lenses of variable power.

In a classical phoropter, different lenses with a fixed, predetermined power may be placed successively in front of each eyes of the subject. For example, lenses with different spheres are placed successively in front of one of the eyes of the subject during successive trials. The sphere is increased by a predetermined step value from one trial to the next. The step value is typically of 0.25 diopter (D), or 0.125 D.

Said subjective test protocol may also use an improved phoropter including lenses of variable power. Such phoropter/variable lenses are for example described in the following documents: US20160331226, US2017027435 or WO2017/021663.

At each trial of the subjective test, corresponding to a current lens placed in front of his eye, the subject is asked to express a visual assessment that corresponds to an indication of a preferred visual state among two visual states presented to him or if he can not decide between the two. The two visual states may correspond to his vision of two different images through the current lens or may correspond to his vision through the previous lens and his vision through the current lens, for example.

In practice, each trial of the subjective test protocol may correspond, for example, to the assessment given by the subject during a duochrome test. During this duochrome test, the subject is presented with an image comprising optotypes displayed on a red background on one side and optotypes displayed on a green background on the other side. If the subject has a better vision of the optotypes on the red background through the current lens, the sphere should be decreased in the next lens presented, and if he has a better vision of the optotypes shown on the green background through the current lens, the sphere should be increased in the next lens presented.

As a variant, at each trial, for the current lens placed in front of his eye, the subject is asked to assess the quality of his vision through the current lens as compared to the previous lens: he is asked if the current lens provides a better vision or a worse vision than the previous lens or if he can not decide between the two. In this last case, the two lenses provide a similar vision quality for the subject.

The subjective test of the state of the art therefore relies on a predetermined standardized protocol. This protocol may use a feature of the subject as an entry for the first trial of the protocol, for example for deciding of the optical features of the test lens first placed in front of the subject. Otherwise, no other customization is provided.

As a consequence, the protocol may take a long time to perform or be inaccurate in the case of specific subjects such as children for example.

SUMMARY OF THE INVENTION

Therefore one object of the invention is to provide a system for determining a subjective value of a magnitude associated with a subjective value of an optical feature of at least a corrective lens adapted to an eye of a subject allowing a more efficient test protocol, reducing the time needed to perform the subjective test and increasing the reliability of the subjective test.

By reliable, it is meant that the subjective value of the optical feature is accurate and repeatable.

The above objects are achieved according to the invention by providing a system for determining a value of a magnitude associated with a subjective value of an optical feature of at least a corrective lens adapted to an eye of a subject, by implementing a subjective test where the subject is asked to describe his visual performance in a plurality of real optical conditions by choosing one descriptive answer among a set of possible descriptive answers, comprising a computer with one or more memory and one or more processor, wherein:

- an initial model giving the probability of each descriptive answer of the set of descriptive answers for each theoretical optical condition of a plurality of theoretical optical conditions is stored in one of said one or more memory of said computer,
- said one or more processor of said computer is programmed to:
  - a) collect the results of said subjective test, performed by asking the subject to describe his visual performance in each real optical condition of said plurality of real optical conditions by choosing, for each real optical condition, one descriptive answer among said set of possible descriptive answers, said results comprising each descriptive answer chosen and the corresponding real optical condition,
  - b) determine the value of said magnitude by taking into account said initial model and each descriptive answer collected.

The magnitude associated with a subjective value of an optical feature of at least a corrective lens adapted to an eye of a subject maybe any kind of magnitude, and in particular:

- the value itself of the optical feature,
- a magnitude determined statistically based on a plurality of values of the optical feature, such as mean, weighted mean, standard deviation,
- an indicator of the level of confidence associated with a measured value of the optical feature.

In step b), said value is determined taking into account said initial model: this is the case as long as at least one trial of the subjective test is performed using said initial model. Said initial model may be used, for example, to determine a modified model used in further trials, to determine a value of a parameter of said subjective test, such as the step value for increasing/decreasing the optical feature of an optical component placed in front of the eye of the subject, and/or directly to determine said value of said magnitude.

Thanks to the system according to the invention, the determination of said magnitude takes into account the initial model that give the probability of each descriptive answer of the set of descriptive answers for each theoretical optical condition of a plurality of theoretical optical conditions. By comparing the real optical conditions to the theoretical conditions, it is therefore possible to determine the most probable answer of the subject in said real optical conditions. Moreover, based on this most probable answer, the subjective test protocol may be modified to be more efficient, by reducing the time needed to perform the subjective test and increasing the reliability of the subjective test.

By determining the initial model based on personal features of the subject, it is moreover possible to adapt the subjective test to the subject.

Other advantageous non limiting features of the system according to the invention are listed hereafter:

- in step b), said computer is programmed to compare said initial model and at least one descriptive answer collected, and determine said value of said magnitude based on this comparison; in particular said computer is programmed to compare said initial model and each descriptive answer collected, and determine said value of said magnitude based on this comparison;
- said initial model comprises at least one of the following: an initial model curve, and initial model formula and an initial model set of data;
- said initial model comprises an initial model curve and said computer is programmed to perform, in step b), the following substeps:
  - plotting at least one collected descriptive answer chosen by the subject against the corresponding real optical condition, and superposing said initial model curve on the plot thus obtained so that the initial model curve fits the plot,
  - determining said value of said magnitude taking into account the relative positions of said initial model curve and said plot;
- said initial model comprises an initial set of data and said computer is programmed to perform, in step b), the following substeps:
  - processing statistically said initial set of data and said collected descriptive answer, and
  - determining said value of said magnitude taking into account this statistical process;
- said computer is programmed to perform, in step b), the following substeps:
  - modifying said initial model to obtain a modified model taking into account at least one descriptive answer of the subject and the corresponding real optical conditions, and
  - comparing said modified model and said descriptive answer collected and determine said value of said magnitude based on this comparison; in particular modifying said initial model to obtain a modified model taking into account each descriptive answer of the subject and the corresponding real optical conditions, and comparing said modified model and each descriptive answer collected and determine said value of said magnitude based on this comparison;
- said modified model comprises at least one of the following: a modified model curve, a modified formula and a modified model set of data;
- said modified model comprises a modified model curve and said computer is programmed to perform, in step b), the following substeps:
  - plotting at least one, possibly each, collected descriptive answer chosen by the subject against the corresponding real optical condition, and superposing said modified model curve on the plot thus obtained so that the modified model curve fits the plot,
  - determining said value of said magnitude taking into account the relative positions of said modified model curve and said plot;
- said modified model comprises an initial set of data and said computer is programmed to perform, in step b), the following substeps:
  - processing statistically said modified set of data and said collected descriptive answer, and
  - determining said value of said magnitude taking into account this statistical process;
- said initial model takes into account one or more personal features of said subject;
- said personal feature include at least a value of a:
  - social parameter: such as age, gender, geographical origin, eyecare history,
  - morphological parameter: such as pupil size, interpupillary distance,
    - optical parameter: such as ametropia type and/or value, astigmatism, eye-lens distance,
  - set-up parameter: such as starting point of the subjective test, type of stimulus, distances for testing far vision or near vision, distance between phoropter and eye,
  - visual parameter: such as acuity, previous answers to subjective test, eye dominance, binocular vision, ocular motility,
  - behavioral parameter: such as: rapidity of previous answers to subjective test, sensitivity to a variation of at least an optical feature of at least an ophthalmic lens;
- said computer is moreover programmed to determine at least an initial parameter value of the subjective test based on a personal feature of the subject;
- said computer is programmed to take into account said initial model to determine said at least an initial parameter value of the subjective test;
- said optical feature of the corrective lens adapted to the subject comprises at least one of the following:
  - spherical power in the zone for far and/or near vision,
  - cylindrical power and/or the axis or a combination thereof, in the zone for far and/or near vision,
  - prism power and/or axis or a combination thereof, in the zone for far and/or near vision,
  - filter transmission, in the zone for far and/or near vision;
- said set of descriptive answer comprises the following answers:
  - better visual performance with first real optical conditions,
  - better visual performance with second real optical conditions,
  - no difference perceived between first and second real optical conditions;
- said initial model is determined statistically based on a reference set of data previously collected while performing said subjective test on a plurality of reference subjects, said reference set of data comprising:
  - personal features of each reference subject, real optical conditions and corresponding answers of each reference subjects;

said initial model is determined based on average values or weighted average values of this reference set of data;

said initial model is determined based on average values or weighted average values of a part of the reference set of data selected based on one or more personal feature of the reference subject and/or said initial model is determined using machine learning algorithms and/or neural networks algorithms;

reference answer plots are obtained by plotting the answers of each reference subject against the corresponding real optical conditions and said initial model is determined based on features of the distribution of said reference answer plots;

said plurality of reference subjects is selected from a group of reference subjects as having one or more personal features identical or similar to the corresponding personal features of the subject;

said computer is programmed to perform said subjective test and to determine said real optical conditions used successively to perform said subjective test taking into account said initial model;

said computer is programmed to perform said subjective test and to determine said real optical conditions used successively to perform said subjective test taking into account said modified model;

said computer is programmed to determine said value of said magnitude based on the position of the initial or modified model curve relative to the plot when this position is determined after a predetermined number of trials or when this position is not modified between two successive trials of the subjective test by more than a predetermined amount;

said computer is programmed to compare each of the collected descriptive answers corresponding to real optical conditions to said initial or modified model and, when this comparison shows that the difference between a specific collected descriptive answer corresponding to specific real optical conditions and the initial, respectively modified, model is over a predetermined threshold, this specific collected descriptive answer is identified as inconsistent;

when a number of inconsistent answers is over a predetermined threshold, the initial or modified model is modified to reduce the number of inconsistent answers.

The invention also relates to a method for determining a value of a magnitude associated with a subjective value of an optical feature of at least a corrective lens adapted to an eye of a subject, through a subjective test where the subject is asked to describe his visual performance in a plurality of real optical conditions by choosing one descriptive answer among a set of possible descriptive answers, comprising the following steps:

i) providing an initial model giving the probability of each descriptive answer of the set of descriptive answers for each theoretical optical condition of a plurality of theoretical optical conditions, j) performing said subjective test by asking the subject to describe his visual performance in each real optical condition of said plurality of real optical conditions by choosing, for each real optical condition, one descriptive answer among said set of possible descriptive answers, k) collecting each descriptive answer of the subject and the corresponding real optical condition, l) determining the value of said magnitude by taking into account said initial model and each descriptive answer collected.

This method is typically implemented by the system according to the invention.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims.

Figure 2:
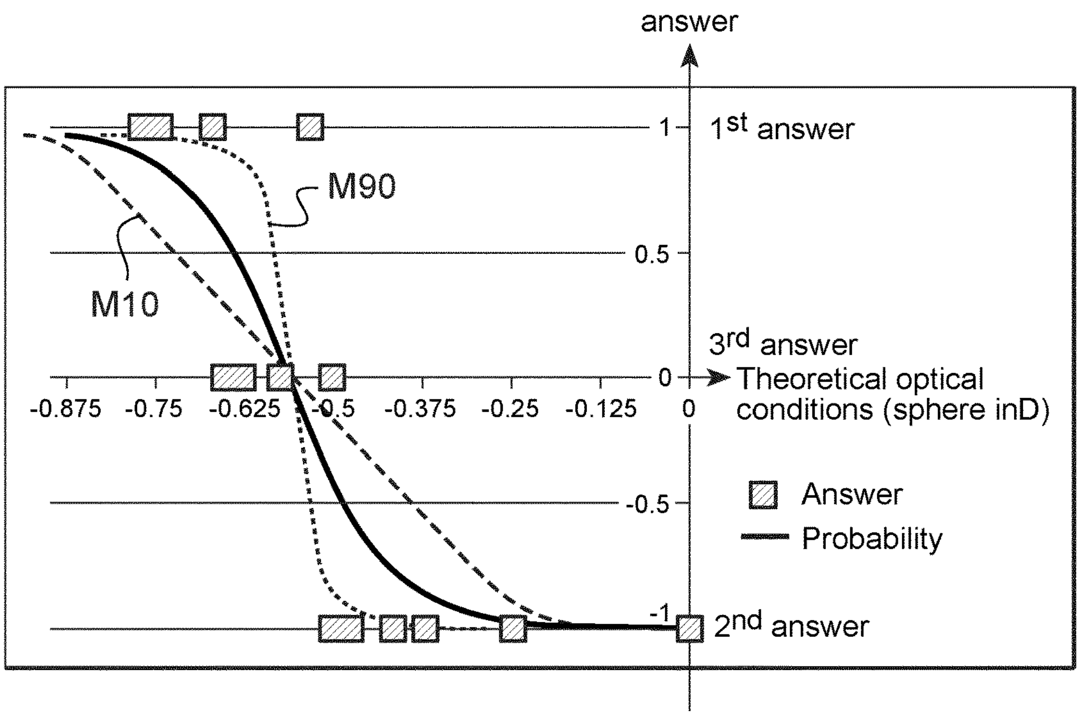

In the accompanying drawings:

FIG. 1 is schematic block representation of an embodiment of the method according to the invention using the device according to the invention, FIG. 2 is a schematic plot of the answers (squares) of a plurality of subject obtained during corresponding subjective tests plotted against theoretical optical conditions linked to the sphere of the lens placed in front of the eye of each subject at each corresponding trial of the subjective tests corrected based on the actual refraction of each subject, with comparison to the graphs (full line and dashed lines) of three different initial models determined based on these data (as explained later, the answer represented by the "0" value corresponds to an answer where the subject distinguishes no difference between two real optical conditions tested);

FIGS. 3 to 7 are schematic plots of answers (squares) of the subject as obtained at successive trials of the subjective test corresponding to real optical conditions (here the sphere in diopters of the test lens), fitted by an initial model curve (full line).

The invention belongs to the field of the conception and manufacture of visual equipment adapted to optical features at least one of the eyes of a subject in order to improve his vision by compensating a visual defect of this eye.

FIG. 1 shows a schematic representation of the steps of an embodiment of the method for determining a value of a magnitude associated with a subjective value of an optical feature of at least a corrective lens adapted to an eye of a subject according to the invention.

The value of said magnitude is determined through a subjective test.

The magnitude associated with a subjective value of an optical feature of at least a corrective lens adapted to an eye of a subject may in particular be:

said subjective value itself of the optical feature, a magnitude determined statistically based on a plurality of subjective values of the optical feature, such as mean, weighted mean, standard deviation, an indicator of a level of confidence associated with said subjective value of the optical feature.

The optical feature of the corrective lens may be any optical feature useful to compensate any kind of visual defect of the subject.

In particular, said optical feature of the corrective lens adapted to the subject comprises at least one of the following:

spherical power in the zone for far and/or near vision of said lens, addition, cylindrical power and/or the axis or a combination thereof, in the zone for far and/or near vision of said lens, prism power and/or axis or a combination thereof, in the zone for far and/or near vision od said lens, filter transmission, in the zone for far and/or near vision of said lens.

The sphere corresponds to the refractive power of the lens given by the spherical component of the shape of the front and back faces of the lens, in diopters.

The cylinder corresponds to the refractive power of the lens given by the cylinder component of the shape of the front and back faces of the lens in diopter.

The axis corresponds to the orientation of the cylinder component of the shape of the lens.

The cylinder power and axis describe the cylinder component of an ophthalmic lens determined to compensate the astigmatism of an eye of the subject. Instead of being determined in the standard polar form with magnitude and orientation decomposition, a vector decomposition of the cylinder component, as described in the document PCT/EP2018/061207 of the Applicant may be used.

The vector decomposition of the cylinder component may be done according to two orthogonal directions J0, J45.

For example, the decomposition along the two J0, J45 directions corresponds to the replacement of the classical sphero-cylindrical notation (Sphere S, Cylinder C, axis) by a triplet of orthogonal values (M, J0, J45) defined as an equivalent spherical lens of power $M=S+C/2$ and two Jackson crossed cylinder lenses one at axis 0° with a power $J0=(-C/2)*\cos(2*axis)$ and the other at axis 45° with a power $J45=(-C/2)*\sin(2*axis)$, as the astigmatism decomposition of the polar form of astigmatism (C, axis).

To be closer to the standard Jackson crossed cylinder procedure, the two orthogonal directions may correspond to the initial astigmatism direction and its perpendicular direction.

The addition may be defined as the difference in sphere between far vision and near vision, for example between the far vision zone and the near vision zone of a progressive lens.

Prism refers to a wedge-shaped optical component. When a ray of light passes through a prism, the ray of light is deviated toward the base of the prism, that is, the larger side of it.

As the corrective lens usually has a non uniform thickness, it behaves like a prism. The subject looking at an object through the lens sees this object as slightly deviated because the image seen appears to originate from the direction of the deviated light ray.

The prism power corresponds to the prismatic displacement of the image in prism Diopter, with one prism Diopter equal one centimeter of displacement over a distance of one meter.

The filter transmission corresponds to the ratio of the intensity of the light coming out of the corrective lens and the intensity of the incident light.

Moreover, subjective values relative to binocular balance, astigmatism, addition, or binocular sphere may also be additionally determined during said subjective test.

After determining the sphere and cylinder components of the correction needed by the subject, it is known that it may be needed to adjust the binocular balance of the eyes. To achieve a comfortable correction of the eyes of the subject, it is indeed useful to ensure that the quality of the images seen through the adapted lenses with the adapted sphere determined is similar on both eyes.

The determination of the value of the adapted sphere of the lens for each eye of the subject may indeed not be performed as accurately for both eyes. It is then useful to compare the quality of the images seen by each eye with the corresponding adapted lens having the adapted sphere, thanks to known methods allowing dissociation of the images seen by each eye, such as using two polarizers oriented at 90°, one of these polarizers being placed in front of each eye. If one of the adapted lenses determined provides a better image than the other, the sphere of this lens may be modified in order to make the quality of the images seen by the subject similar.

The corresponding optical feature may then be equal to the difference between the spheres of both lenses.

It may also be equal to the difference between the interval between the sphere of both lenses initially determined before the binocular balance test and the interval between the spheres of both lenses after the binocular balance test.

After adjusting the binocular balance, the binocular sphere may be adjusted. Based on the values of sphere determined previously, for example after the binocular balance test, the spheres of both lenses are varied simultaneously with the same increment, and the quality of the binocular vision is assessed by the subject. The subject is then asked to compare the quality of the image seen when varying both spheres.

More precisely, according the method of the invention, it comprises the following steps:

i) providing an initial model giving the probability of each descriptive answer of the set of descriptive answers for each theoretical optical condition of a plurality of theoretical optical conditions, j) performing said subjective test by asking the subject to describe his visual performance in each real optical condition of said plurality of real optical conditions by choosing, for each real optical condition, one descriptive answer among said set of possible descriptive answers, k) collecting each descriptive answer of the subject and the corresponding real optical condition, l) determining the value of said magnitude by taking into account said initial model and each descriptive answer collected.

This method is implemented by a system for determining a value of a magnitude associated with a subjective value of an optical feature of at least a corrective lens adapted to an eye of a subject according to the invention.

This system comprises a computer with one or more memory and one or more processor.

According to the invention, an initial model giving the probability of each descriptive answer of the set of descriptive answers for each theoretical optical condition of a plurality of theoretical optical conditions is stored in one of said one or more memory of said computer.

Said one or more memory of said computer may comprise a permanent or a transitory memory.

This memory may be local or distant. Said memory may be housed with said processor or may be accessed remotely thanks to a network cable (wired) or with a wireless connection. Therefore said initial model may be stored in a local memory of said computer or retrieved from a server/cloud.

In a preliminary step of the method according to the invention, said initial model is determined (block 300 of FIG. 1).

The initial model gives the probability of each descriptive answer of the set of descriptive answers for each theoretical optical condition of a plurality of theoretical optical conditions.

Said initial model may comprise at least one of the following: an initial model curve, an initial model formula between answers and theoretical optical conditions and an initial model set of data.

In particular, said initial model may be continuous in the case of a curve or formula or discontinuous in the case of a set of data.

The initial model curve may correspond to the graphical representation of a corresponding initial model formula linking answers and theoretical optical conditions or initial model set of data or may be determined based on such an initial model set of data.

Said initial model curve or formula or set of data is for example determined statistically based on a reference set of data previously collected while performing said subjective test on a plurality of reference subjects, said reference set of data comprising real optical conditions and corresponding answers of each subjective test performed with each reference subjects.

In said preliminary step of the method according to the invention, said set of data is acquired (block 100 of FIG. 1).

Preferably, each answer for every corrective value tested, for all tests performed, such as classical refraction test, duochrome test, Jackson Cross Cylinder test, binocular balance test, is collected and may be taken into account to determine said initial model.

The reference set of data also preferably comprises at least one personal feature of each reference subject, saved in relation to the other data relative to this reference subject.

Said personal feature include at least a value of a:

social parameter, such as age, gender, geographical origin, eyecare history (past prescriptions, ocular diseases/problems . . . ), morphological parameter, such as pupil size, interpupillar distance, optical parameter, such as ametropic type and/or value, in particular sphere refraction value, cylinder refraction value, cylinder axis, astigmatism, eye-lens distance, set-up parameter, such as starting point of the subjective test, type of stimulus, distances for testing far vision or near vision, distance between phoropter and eye, visual parameter, such as acuity, previous answers to subjective test, eye dominance, binocular vision, or ocular motility, behavioral parameter, such as: rapidity of previous answers to subjective test, sensitivity to a variation of at least an optical feature of at least an ophthalmic lens.

Other information relative to the reference subject are preferably collected in said reference set of data, such as final refraction or final optical feature determined through each test performed.

The reference set of data is for example collected by saving the above mentioned data of each reference subject after each subjective test performed.

Data may be gathered automatically from devices used for performing the subjective tests anywhere in the world, and programmed to transmit these data to said computer.

In an embodiment, said initial model is determined based on statistical features of the reference set of data.

In particular, said initial model is determined based on average values or weighted average values of the reference set of data.

This means that the initial model curve or formula or set of data is determined by fitting a modified data set comprising average values or weighted average values of the reference set of data.

For example, the three different possible answers of the subjective test performed may be associated with a numerical value, and these values may be averaged for fixed real optical conditions.

The possible answers are for example:

better visual performance with first real optical conditions, coded for example as "1", that is to say, represented on FIG. 2 by the ordinate value 1, better visual performance with second real optical conditions, coded for example as "−1", that is to say, represented on FIG. 2 by the ordinate value −1 no difference perceived between first and second real optical conditions, coded for example as "0", that is to say, represented on FIG. 2 by the ordinate value 0.

In the case where the initial model curve or formula or set of data is determined by fitting a modified data set comprising average values or weighted average values of the reference set of data, if for given a sphere value 10 answers are obtained corresponding to the value −1, 8 answers corresponding to the value 0 and 2 answers corresponding to the value +1, the average value of the answer that will be associated with the given sphere value is −0.4 (−40% for a percentage scale). The averaged answers may be given by the same subject or by different subjects. Finally, the averaged values of the set of data are not a priori equal to −1, 0 or 1 but are representative of the probability to obtain 1, 0 or −1 answers.

It is also possible to determine the initial model based on distribution envelopes of the reference set of data. For example, reference answer plots are obtained by plotting the answers of each reference subject against the corresponding real optical conditions and said initial model is determined based on features of the distribution of said reference answer plots.

Distribution envelopes may for example be defined as comprising data within a given percentile or data located at a given distance from the average data. For example, for a set of reference data, all the data collected for a specific real optical condition are distributed around an averaged or a median value. The median value corresponds to a distribution of 50%: 50% of the values collected for this real optical condition are above the median value and 50% is below.

Other statistically interesting values may be for example defined by values at 10% and 90% of the distribution. 90% of the values collected for this real optical condition is above the value at 10% of the distribution and 10% is below; 10% of the values collected for this real optical condition is above the value at 90% of the distribution and 90% is below.

Examples of different initial models obtained by using different parts of the distribution of the reference set of data are represented on FIG. 2.

The curve in full line represents the initial model obtained by taking into account the data at 50% of the distribution.

The two curves in dashed lines represent the initial models obtained by taking into account the values at 10% (curve M10) and the values at 90% (curve M90) of the distribution of data. In the case of FIG. 2, the data represented is corrected according to the description hereafter.

Any other distribution of the reference set of data, corrected or not, may also be used. For example, values at a percentage of 25% (first quartile) or values at a percentage of 75% (third quartile) could be used.

In an embodiment, the initial model takes into account the descriptive answers given by all the reference subjects without selecting reference subjects based on their personal features.

In this case, the reference set of data may need to be corrected to take into account the differences between the personal features of the reference subjects. The initial model is then determined based on the corrected reference set of data.

For example, the theoretical optical conditions of said initial model are linked to the optical component placed in front of the subject when the answer plotted in ordinate was given by the reference subject. These theoretical optical conditions may be the value of an optical feature of the lens placed in front of the subject, or deduced from the value of this optical feature, for example by applying an offset or a multiplicative factor.

An example is described hereafter as to how the reference data of reference subjects having different actual sphere refraction may be taken into account to determine the initial model.

In order to do so, the theoretical optical conditions of the initial model are defined relative to the actual refraction of each reference subject. For example, the theoretical optical conditions may correspond to the real optical conditions of the reference set of data with an offset. The offset is calculated to center the data on a predetermined value of refraction. The initial model is then determined on the basis of corrected real optical conditions corresponding to the real optical conditions with an offset.

For example, in practice, the subjective test for the reference subject is first performed as it is usually the case according to the methods known from the man skilled in the art. An actual value of the refraction of the reference subject is determined through this test.

Then, the actual value of the refraction is subtracted from the value of the optical feature of the lenses used in each trial of the subjective test, in order to obtain the answers of the reference subject in theoretical optical conditions relative to the actual value of the refraction. It is then possible to compare the reference data obtained for each reference subject, and in particular, to average them.

The embodiments described here may of course be combined, and the initial model may be determined based on data of a selected group of subject that are corrected to be compared.

An example of an initial model obtained with such a protocol is shown on FIG. 2.

FIG. 2 shows the values of the answers of different reference subjects centered on their actual value of the refraction and overlaid to be centered at −0.5 D.

More precisely, the ordinate shows the three different possible answers of the subjective test performed.

These possible answers are for example, as mentioned before:

- first choice or answer: better visual performance with first real optical conditions, coded as “1”,
- second choice or answer: better visual performance with second real optical conditions, coded as “−1”,
- third choice or answer: no difference perceived between first and second real optical conditions, coded as “0”.

The abscissa shows the theoretical optical conditions.

In the example of FIG. 2, the theoretical optical conditions are determined based on the value of the sphere of the lens placed in front of the reference subject, as explained below.

A group of reference subjects having a refraction of −0.5 D plus or minus 0.2 D is considered.

In this example, the answers of all the reference subjects of this groups are centered about −0.5 D. This means that, for a reference subject of this group whose refraction was finally determined to be −0.53 D, the values of the answers acquired are plotted, or saved in correspondence with, values of the theoretical optical conditions corresponding to the real optical conditions used during the subjective test, +0.03 D, thereby centering the results at −0.5 D.

Thereby, a corrected reference set of data comprising the answers and the corresponding theoretical optical conditions, is generated.

The corrected reference set of data is represented by the squares plotted on FIG. 2. The initial model giving the probability of each descriptive answer of the set of descriptive answers for each theoretical optical conditions of a plurality of theoretical optical conditions is here obtained based on the corrected reference set of data by determining a curve or a formula fitting the corrected reference set of data.

In the example described here and shown on the figures, the general formula used for the fitting is the one of a sigmoid of general formula:

$$(1-2/(1+e^{(-s*(x-x0))}))$$, using a RMS minimization.

In the above mentioned general formula of the sigmoid, S is the maximum slope of the sigmoid, x0 the relative position of the sigmoid, x the abscissas of the fitted data (real optical condition value). RMS is defined as the root mean square of the difference between the ordinates given by the answer from the data and given by the formula trying to be fitted.

Other general formula may be used to determine the initial model by fitting or interpolating the reference data, for example a step function, linear, polynomial or any other kind of function.

On the example initial model shown, the initial model is scaled to vary between 1, corresponding to 100% probability of first choice or answer, and −1 corresponding to 100% probability of second choice or answer.

In a general manner, the slope of the part of the initial model curve comprised between 1 and −1 ordinates and crossing the abscissa axis is bigger for subject with higher sensitivity to a variation of the real optical conditions, for example to variation of refraction power of the lens placed in front of their eye and lower for subjects with lower sensitivity.

Alternatively, the initial model could also comprise a model set of data comprising the average/weighted average value of the answer associated to the corresponding theoretical optical conditions.

Preferably, the initial model is determined taking into account at least a personal feature of said subject.

In the embodiment of the method according to the invention represented on FIG. 1, at least a personal feature of the subject is acquired (block 200 of FIG. 1) during said preliminary step.

Said personal feature of said subject may be any of the personal features listed above.

Preferably, this personal feature is relative to the type of visual defect of the subject.

It may also be relative to the age of the subject.

Said personal features may for example comprise the age, and/or the type/value of ametropia, and/or the distance between eye and lens of the eyewear. The type of subjective test performed may also be taken into account.

For example, different initial models are determined for subjects with myopia, hypermetropia, for subjects with an age within a predetermined range, etc. . . .

Preferably, the initial model is determined taking into account a plurality of personal features of said subject. The initial model is for example determined through successive step, each step taking into account one personal feature.

The initial model may then be obtained using supervised learning (for example a decision tree or a neural network) with for all data collected on said reference subject to build the learning phase:

for entries: the personal features and the value of the optical feature at the corresponding trial of the subjective test (sphere, cylinder, axis . . . )

for output: the response (or the probability of certitude in the answer) associated to each trial. For example, choice 1 for sure (100% probability), choice 1 maybe (60% probability), no choice (0% probability), choice 2 maybe (−60% probability), choice 2 for sure (−100% probability). Said output could be a discrete or continuous variable.

In particular, it is possible to determine an initial model associated to each personal feature, or a set of different initial model, with a probability associated to each initial model in view of the personal feature of the subject, in particular, in view of the sensitivity of the subject to a variation of the real optical conditions used, in view of his age and/or in view of his expected ametropia (nature and/or value).

For example, in the case of the initial model obtained by fitting reference data with a sigmoid general formula, the slope of the part of the initial model curve crossing the abscissa axis may be adjusted depending on the sensitivity of the subject to a variation of the real optical conditions, for example to a variation of at least an optical feature of at least an ophthalmic lens.

The optical feature corresponds here to the real optical conditions of the subjective test.

Subjects with higher sensitivity to the variation of said optical feature will indeed benefit of a higher slope in said initial model, as it will allow performing said subjective test quicker.

The slope of the initial model may also be adjusted depending on the age of the subject, his level of understanding of the test (for example depending on whether or not he speaks fluently the language of the test) or his level of tiredness at the moment of the test. Older and younger subjects or subjects with a lack of understanding and in general tired subjects will benefit from using an initial model with a lower slope that will induce a more progressive test giving more trials allowing checking the answers obtained.

Finally, the slope of the initial model may also be adjusted depending on the ametropia of the subject. For example, for subjects with myopia and/or astigmatism: the higher the value of the correction needed by the subject, the lower the slope of the initial model should be.

Moreover, the evolution of the answers of the subject during the subjective test may also be taken into account.

Some subjects indeed will provide different answers when the progression of the real optical conditions is in one direction or the other. More precisely, in the case of varying the optical power of a lens, answers of the subject while decreasing the optical power may be different from the answers while increasing the optical power.

The answers at the end of the subjective test may be closer to the expected answers according to the initial model than answers at the beginning of the subjective test because of a training effect.

To the opposite, for some subjects, answers at the end of the subjective test may be further away from the expected answers according to the initial model than answers at the beginning of the subjective test because of tiredness of the subject.

The behavior of the subject relative to training effect/tiredness during the subjective test is also a personal feature that may be taken into account while determining the initial model (or further modified models) by giving a different weight to the answers collected in the reference data based on the period of time of the subjective test when they were collected. Of course, the answer with better reliability (no tiredness, after training) will be assigned a higher weight.

This process for determining the initial model is useful especially when the personal features taken into account are numerous.

The selection among all the personal features and the weight of each personal feature could also be determined using machine learning algorithm and/or neural networks methods.

It is possible to use this process on a selected group of reference subjects.

In an embodiment, said initial model is determined based on values, average values or weighted average values of a part of the reference set of data.

The part of the reference set of data taken into account is preferably selected based on one or more reference personal feature of the reference subjects.

More precisely, the part of the reference set of data taken into account is selected in order to keep the data obtained for reference subjects whose said one or more reference personal feature match the corresponding personal feature of the subject whose eyes are currently tested.

The reference personal feature of the reference subject may be the same as the personal feature of the subject or may be in a predefined range about the personal feature of the subject.

In other words, said plurality of reference subjects is selected from a group of reference subjects having one or more personal features identical or similar to the corresponding personal features of the subject.

For example, for a myopic subject, the initial model is determined by taking into account a reference set of data gathered from selected myopic reference subjects. For a myopic subject with a previously known refraction of −1 D, the initial model is determined by taking into account a reference set of data gathered from selected myopic reference subjects having a final refraction determined to be −1 D or a final refraction determined to be between −0.9 D and −1.1 D or between −0.5 D and −1.5 D or 0 D and −2 D. The data of the selected reference subjects may be corrected as described before to be centered at the actual refraction or visual defect of each reference subject.

The initial model may then be directly used with the data collected during a subjective test performed on said subject to determine said magnitude.

However, in a preferred embodiment, said subjective test is adjusted based on said initial model (block 400 of FIG. 1).

In practice, said computer is programmed to determine at least an initial parameter value of the subjective test based on a personal feature of the subject.

Personal features such as age, sensitivity of the subject to a variation of an optical feature of the lens, level of understanding and/or of tiredness, nature and value of ametropia, may in particular be taken into account.

When the subject is determined to be less likely to accommodate, which is for example the case for older subjects (adults), an initial value of the refraction of the eye of the subject, for example objectively measured with an autorefractor, will be used as a starting value for the subjective test, without any modification.

When the subject is determined to be prone to accommodating, for example for younger subjects (children), hypermetrope subjects or tired subjects, said initial value of the refraction of the subject will be increased by an added value. The higher the tendency to accommodate of the subject is determined, the higher said added value to the initial value of refraction is determined.

For example, the initial value of the optical feature of the optical component placed in front of the eye of the subject or the initial value of the step value for increasing or decreasing this optical feature may be determined taking into account said initial model.

For example, in the situation where the initial model based on averaged data of FIG. 2 is taken into account, if the first trial uses an optical lens of refraction power equal to −0.375 D, the answer 2 is expected based on the initial model. A second trial will be performed with a −0.75 D optical lens and the answer 1 is expected. If the answers given by the subject matches the expected answers, the initial model is confirmed; otherwise it will be adjusted, for example modified to take into account the answers of the subject.

In a general manner, based on the initial model and the initial parameter value (for example the values of a past prescription), the computer is programmed to perform the two first trials with values of the real optical conditions such that one answer 1 and one answer 2 is obtained while performing the two successive first trials. This allows reducing the total number of trials needed.

Said computer is programmed to take into account said initial model to determine said at least an initial parameter value of the subjective test.

The subjective test is then performed on said subject.

According to the invention, said one or more processor of said computer is programmed to:

a) collect the results of said subjective test, performed by asking the subject to describe his visual performance in each real optical condition of said plurality of real optical conditions by choosing, for each real optical condition, one descriptive answer among said set of possible descriptive answers, said results comprising each descriptive answer chosen and the corresponding real optical condition (block 500 of FIG. 1), b) determine the value of said magnitude by taking into account said initial model and each descriptive answer collected (blocks 800, 900 of FIG. 1).

Step a)

During said subjective test, the subject is asked to describe his visual performance in a plurality of real optical conditions by choosing one descriptive answer among said set of possible descriptive answers.

This subjective test may be performed within the method according to the invention or independently from it.

Each real optical condition of said plurality of real optical conditions correspond typically to a given value of an optical feature, such as sphere, cylinder, axis or transmission coefficient, of an optical component such as a test filter or test lens placed in front of the eye of the subject.

The subjective test is usually performed by using a specific device known as a "phoropter" This phoropter comprises either at least one test optical component with variable optical feature, such as a test lens with variable optical power or a plurality of test optical component with different fixed, predetermined optical features, such as a plurality of lenses with different fixed, predetermined optical powers and at least one support adapted to support the test optical component or one of said plurality of test optical components. Said support is adapted to be positioned in front of the head of the subject in order to place the test optical component supported by said support in front of a eye of the subject to be tested.

Variable lenses are for example described in the following documents: US20160331226, US2017027435 or WO2017/021663.

The device may also comprise other test optical components with different optical features, such as spherical lenses, cylindrical lenses, prism, linear or circular polarized filters, colored filters, transmission filters, stenopeic holes, badal system, mirrors, active lenses, deformable mirrors, SLM (spatial light modulators), Alvarez lenses . . . .

In practice, the subject's vision is tested during a subjective test protocol, using said phoropter to place successively in front of at least one of the eye of the subject test optical components such as lenses with different values of said optical feature.

In the case of test lenses, the optical power is increased or decreased by a predetermined step value from one step of the subjective test to the next. The step value is typically of 0.25 diopter (D), or 0.125 D. The successive steps of the subjective test are here called "trials".

For each test lens placed in front of his eye, the subject is asked to express a visual assessment that corresponds to an indication of a preferred visual state among two visual states presented to him or if he can not decide between the two. The two visual states may correspond for example to his vision through the previous lens and his vision through the current lens or may correspond to his vision of two different images through the current lens.

In practice, this part of the test protocol may correspond, for example, to the assessment given by the subject during a duochrome test. During this duochrome test, the subject is presented with an image comprising optotypes displayed on a red background on one side and optotypes displayed on a green background on the other side. If the subject has a better vision of the optotypes on the red background through the current lens, the sphere should be decreased in the next lens presented, and if he has a better vision of the optotypes shown on the green background through the current lens, the sphere should be increased in the next lens presented.

As a variant, for each current lens placed in front of his eye, the subject is asked to assess the quality of his vision through the current lens as compared to the previous lens: he is asked if the current lens provides a better vision or a worse vision than the previous lens or if he can not decide between the two. In this last case, the two lenses provide a similar vision quality for the subject.

The phoropter may be part of the device according to the invention described here or distinct from it. In this last case, it may comprise communication means with the device according to the invention.

As mentioned before, in a general manner, said set of descriptive answers comprises for example the following answers:

better visual performance with first real optical conditions, better visual performance with second real optical conditions, no difference perceived between first and second real optical conditions.

The first and second real optical conditions may correspond to the observation of the same image with different test optical component having different values of the optical feature or to the observation of different images with the same test optical component, such as an image comprising optotypes displayed on a red background on one side and optotypes displayed on a green background.

Step b)

In step b), said computer is for example programmed to compare said initial model and each descriptive answer collected, and determine said value of said magnitude based on this comparison.

In the case where the initial model comprises an initial model curve, said computer is programmed to perform, in step b), the following substeps:

b1) plotting each collected descriptive answer chosen by the subject against the corresponding real optical condition, and superposing said initial model curve on the plot thus obtained so that the initial model curve fits the plot, b2) determining said value of said magnitude taking into account the relative positions of said initial model curve and said plot.

The step of plotting the collected descriptive answer does not imply here that this plot is in any way displayed. The plot and/or other curves may or may not be displayed for the user and/or subject to see.

In an embodiment, said subjective value of an optical feature of at least a corrective lens adapted to an eye of a subject is directly determined by comparing the answers collected for said subject with said initial model.

In step b1), the initial model is not modified to fit the plot, but the relative positions of the model curve and plot is modified in order to minimize the distance between the model curve and the plot, in a global manner. The distance is for example minimized using quadratic optimization.

With the initial model as determined in the example of FIG. 2, the placement of the initial model relative to the data collected for a subject may give the actual refraction of said subject at the intersection between said initial model and the abscissa.

As a variant, said computer is programmed to perform said subjective test. In the embodiment of FIG. 1, block 500 corresponds to performing the subjective test and collecting the corresponding data.

In this case, said computer is programmed to adjust the parameters of the subjective test taking into account said initial model (block 400 of FIG. 1). It is for example programmed to determine said real optical conditions used successively to perform said subjective test taking into account said initial model.

Advantageously, step b1) is performed at each trial of said subjective test, in other words, for each answer given by the subject. For each new answer given by the subject, this answer is added to the plot and the relative positions of the model curve and plot is modified in order to minimize the distance between the model curve and the plot, in a global manner. Then, at each trial, an intermediary value of said magnitude may be determined, and a parameter of the subjective test may be modified before performing the next trial. In particular, the step value between two successive values of the optical feature of the test lens used during the test may be adjusted. Alternatively, the next value of the optical feature of the test lens may be directly determined.

The subjective test is then adjusted to take into account the data already collected for said subject (arrow 501 of FIG. 1).

An example of this process is shown on FIGS. 3 to 7. On these figures, the squares show the position of a plotted data of the subject: answer given at corresponding real optical conditions, here the sphere in diopters of the test lens. The initial model is represented by the curved line.

Figure 3:
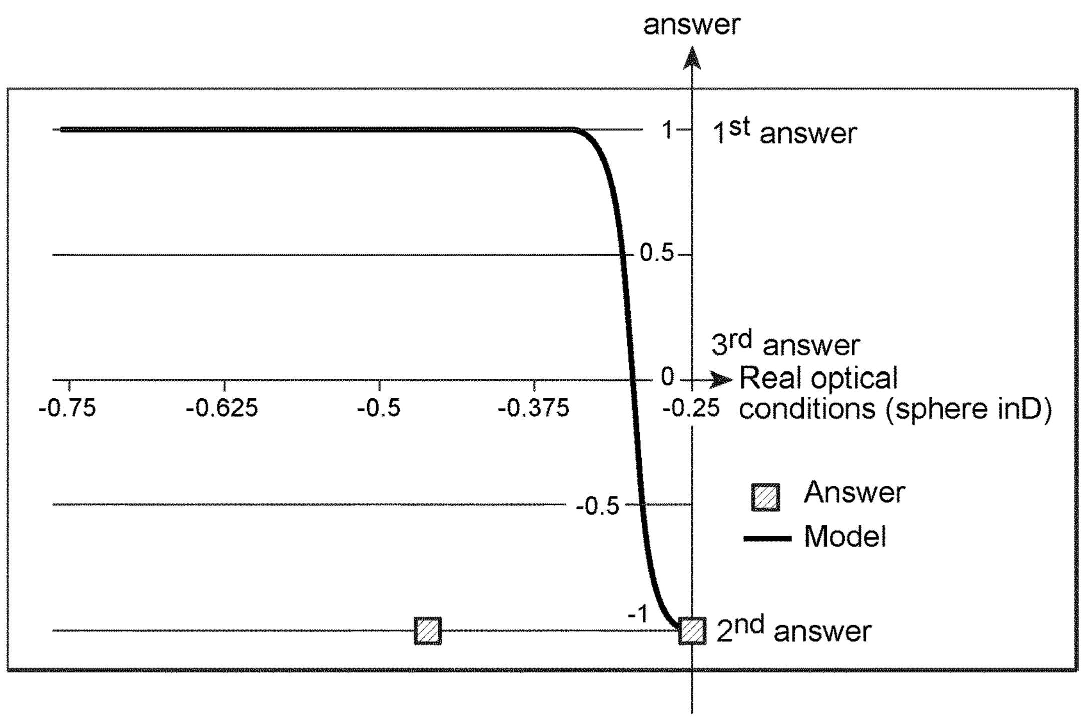

FIG. 3 shows the result of the first trial with only one answer of the subject. The initial model is placed to go through this single point. The position of the initial model curve is therefore uncertain.

Figure 4:
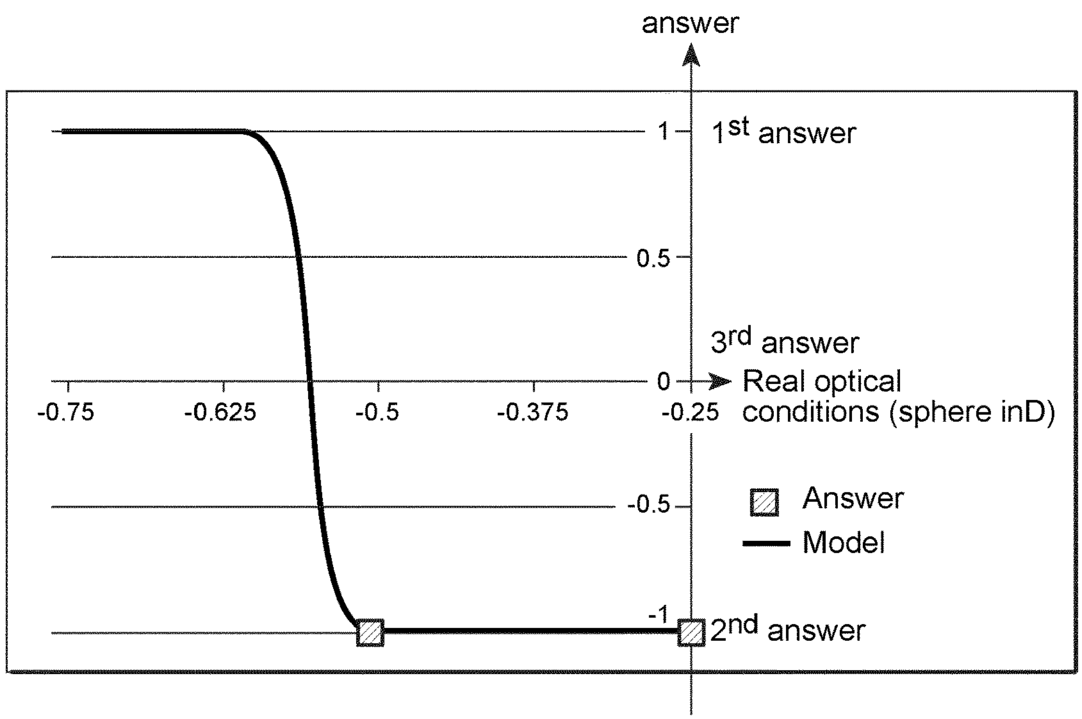
Figure 5:
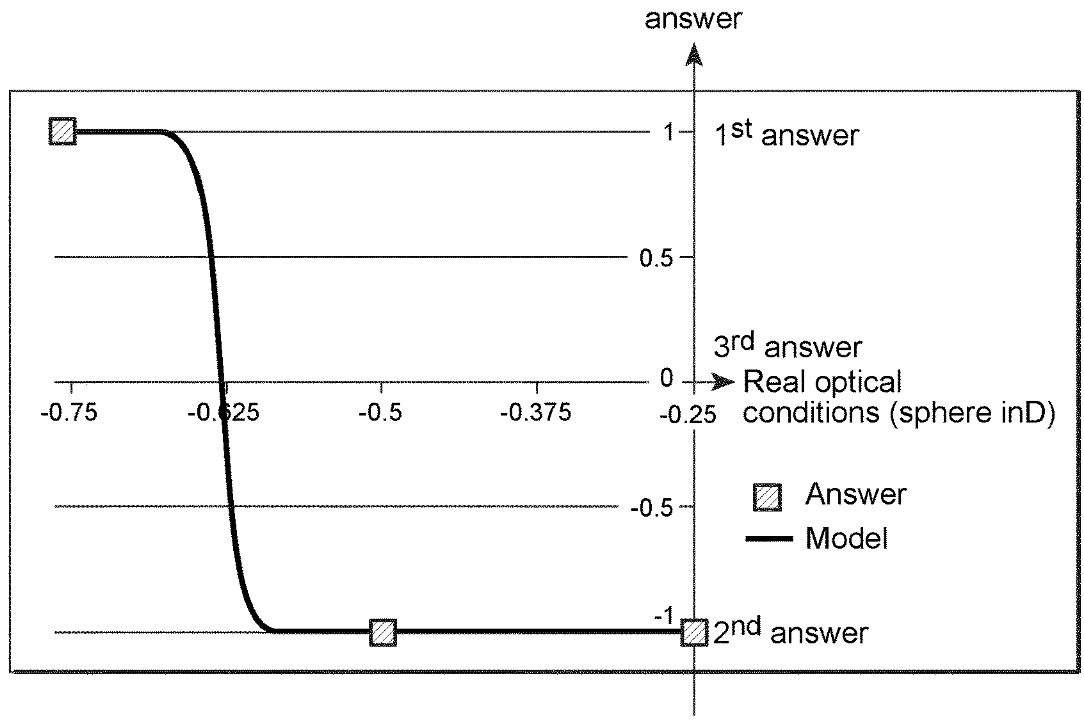

After a second trial, a second answer is plotted and the initial model curve is moved to fit the plot (FIG. 4).

After a third trial, a third answer is plotted and the initial model curve is moved accordingly.

Figure 6:
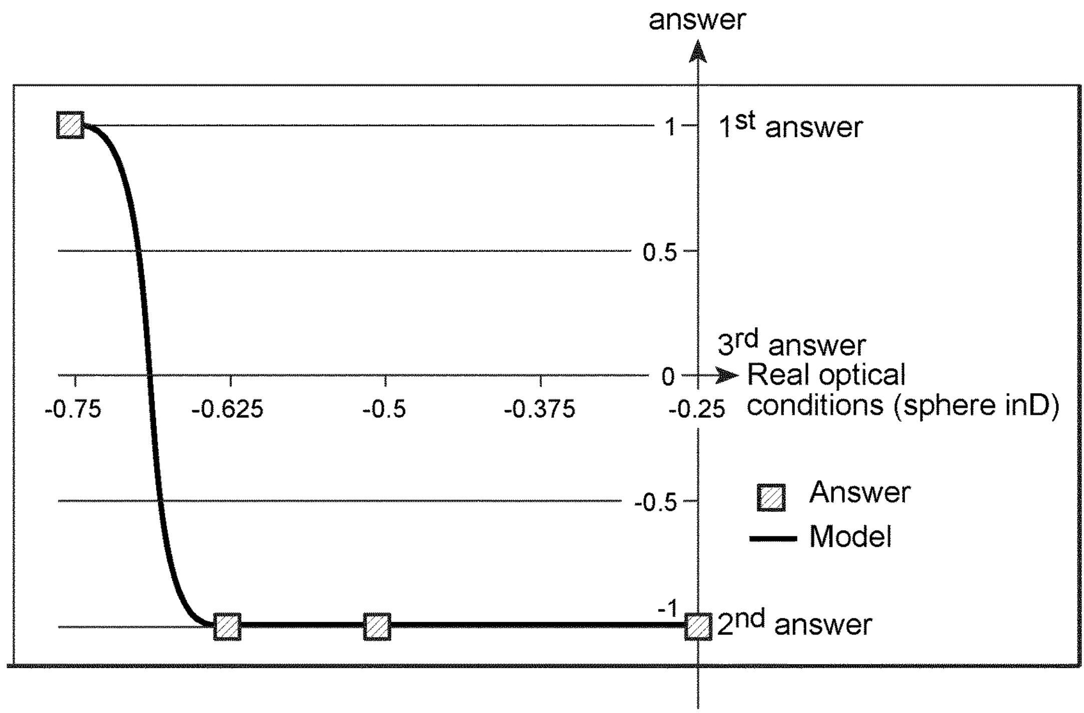
Figure 7:
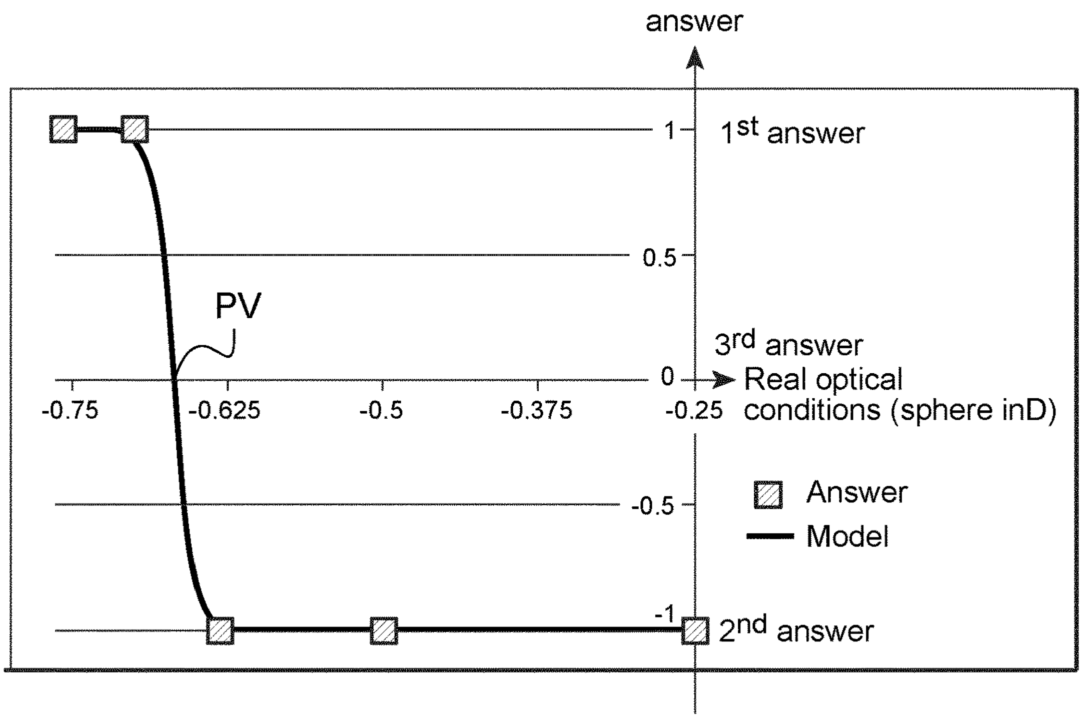

FIGS. 6 and 7 show the corresponding next two trials.

The intersection PV of the initial model curve with the abscissa gives a predicted value of the sphere refraction of the eye (FIG. 7).

It is therefore possible to adjust the diopter variation step value of the test lens in order for the next test lens to have a sphere close to the predicted value of the sphere refraction of the eye.

Said computer may be programmed to determine said value of said magnitude based on the position of the initial model curve relative to the plot when this position is determined with a predetermined number of trials or when this position is not modified between two successive trials of the subjective test by more than a predetermined amount. For example, when this position is determined after a number of trials of at least 4, 10 or 20, or when this position is not modified between two successive trials of the subjective test by more than 0.25 D, 0.12 D or 0.06 D.

The use of the initial model allows obtaining an accurate position of the curve quickly.

In the case where the initial model comprises an initial set of data, said computer is programmed to perform, in step b), the following substeps:

processing statistically said initial set of data and said collected descriptive answer, and determining said value of said magnitude taking into account this statistical process. In practice a law describing the variation of the reference set of data is determined by said statistical process, and this law is then applied to the answers of the subject during the subjective test.

According to an advantageous feature of the device and method according to the invention, said initial model may be modified at any trial of the subjective test, that is, with every new test optical component proposed to the subject (block 600 of FIG. 1).

In particular, said initial model may be modified, at any trial of the subjective test, based on at least one of the previous answer collected for said subject (arrow 502 of FIG. 1).

In an embodiment, the initial model may have been determined by taking into account a first personal feature of the subject. At any trial of the subjective test, it may be modified to take into account a second personal feature of the subject, different from the first personal feature. The second personal feature may be taken into account in addition to the first personal feature, or instead of the first personal feature.

For example, the initial model may be modified in real time to take into account the behavior of the subject while responding: facial features, facial expressions, voice, hesitation, time elapsed between the presentation of each new real optical conditions and the answer of the subject.

Regarding the time elapsed between the presentation of each new real optical conditions and the answer of the subject, it could be compared to a threshold value: if the time elapsed is over said threshold, the answer is not taken into account.

In an embodiment, the initial model may be modified to take into account the answers collected for said subject. The subject is then included in the reference subjects whose answers are used to determine the model.

The modified model thus obtained is then used to determine said magnitude.

In this case, said computer is programmed to perform, in step b), the following substeps:

modify said initial model to obtain a modified model taking into account each descriptive answer of the subject and the corresponding real optical conditions, and compare (block 700 of FIG. 1) said modified model and each descriptive answer collected and determine said value of said magnitude based on this comparison.

Said modified model is determined and used just as the initial model as described earlier. It may comprise at least one of the following: a modified model curve, a modified model formula between answers and theoretical optical conditions and a modified model set of data.

When said modified model comprises a modified model curve, said computer is programmed to perform, in step b), the following substeps:

plotting each collected descriptive answer chosen by the subject against the corresponding real optical condition, and superposing said modified model curve on the plot thus obtained so that the modified model curve fits the plot, determining said value of said magnitude taking into account the relative positions of said modified model curve and said plot.

Alternatively, if said modified model comprises a modified set of data, said computer is programmed to perform, in step b), the following substeps:

processing statistically said modified set of data and said collected descriptive answer, and determining said value of said magnitude taking into account this statistical process.

In practice, said computer is programmed to determine at least one of said real optical conditions used to perform said subjective test by taking into account said modified model. In particular, said computer may be programmed to determine each of said real optical conditions used to perform the posterior trials of said subjective test by taking into account said modified model.

Said computer is programmed to determine said value of said magnitude based on the position of the modified model curve relative to the plot when this position is determined with a predetermined number of trials or when this position is not modified between two successive trials of the subjective test by more than a predetermined amount (block 800 of FIG. 1).

Moreover, said computer is programmed to compare each of the collected descriptive answers corresponding to real optical conditions to said initial or modified model and, when this comparison shows that the difference between a specific collected descriptive answer corresponding to specific real optical conditions and the initial, respectively modified, model is over a predetermined threshold, this specific collected descriptive answer is identified as inconsistent (block 900 of FIG. 1).

In particular, false answers or uncertain answers could be detected using a criterion that calculates the distance from the curve of the initial or modified model. When the distance between the plot of the answer and the curve of said initial or modified model is higher than a predetermined threshold value or higher than if it was a "don't know" answer, the answer is identified as inconsistent.

An indicator of the level of confidence associated with each subjective value measured of the optical feature may therefore be determined based on this distance between the plot of the answer and the curve of said initial or modified model. The indicator for example gives an indication of a higher level of confidence for answers corresponding to plots that are closer to the model.

When an inconsistent answer is thus detected, an alert may be emitted to the destination of the operator of the subjective test. The inconsistent answer is preferably not taken into account for determining said magnitude.

Preferably, the trial of the subjective test for which the inconsistent answer was collected is repeated and another answer is collected to replace the inconsistent answer not taken into account (arrow 901 of FIG. 1).

Preferably, when a number of inconsistent answers detected during a subjective test is over a predetermined threshold, the initial or modified model is modified to reduce the number of inconsistent answers (arrow 902 of FIG. 1).

Then the initial or modified model is changed. For example, a model based on average reference set of data may be changed for a model based on the distribution of the reference set of data or a model based on personal features of the subject may be changed to a more general model based on all reference data.

A typical behavior may be detected. For example, younger subjects tend to answer faster than older subjects. If a young subject is slower, it may be due to a particular problem or misunderstanding of this subject.

In a general manner, during the subjective test, the initial value of the real optical conditions is determined taking into account the personal features of the subject, such as past prescriptions if any, and taking into account the initial model selected or determined for this subject. The next values of the real optical conditions are determined by the computer based on the initial model.

For example, as already mentioned, the computer is programmed to perform the two first trials with values of the real optical conditions such that one answer 1 and one answer 2 is obtained while performing the two successive first trials.

The correspondence between actual answers and expected answers according to the initial model is monitored. The actual answer of the subject for a given real optical condition is compared to the expected answer based on the initial model for the corresponding theoretical optical conditions.

In the case where the actual answers match the expected answers, the initial model may be kept or modified for further improvements. It may be considered that the actual answers match the expected answers when the number of actual answers different from the expected answer is below a first discrepancy threshold.

In the case where the actual answers differ from the expected answers, either the use of the initial model is stopped and the subjective step resume in a traditional manner, or the initial model is modified. It may be considered that the actual answers differ from the expected answers when the number of actual answers different from the expected answer is above a second discrepancy threshold.

According to a first possibility, another predetermined model may be tried.

According to a second possibility, the data currently being collected for said subject may be added to the reference data and the modified model is determined based on this updated reference data comprising the collected data for the subject.

According to a third possibility, a new model may be determined on the basis of the data collected for said subject, current and past data. This last solution is especially useful when past data is available.

The invention indeed also allows taking into account data of a past eye exam, which allows understanding better the evolution of the behavior. This may be used in the prevention and/or detection of cataract evolution or in the prevention and/or detection of other evolutionary refraction defects (myopia) or pathology (degeneration of the macula according to age . . . ). For example, determining that a past initial model used for a subject with success is not at all adapted to this subject later may be the sign of a new problem such as cataract.

The invention claimed is:

1. A system for determining a value of a magnitude associated with a subjective value of an optical feature of a corrective lens adapted to an eye of a subject, said optical feature being applicable to compensate for a visual defect of the subject, by implementing a subjective test where the subject is asked to describe his visual performance in a plurality of real optical conditions by choosing one descriptive answer among a set of possible descriptive answers, each real optical condition of said plurality of real optical conditions comprising a value of an other optical feature of an optical component placed in front of the eye of the subject, the system comprising:

a computer with one or more memory and one or more processor, wherein:

an initial model giving a probability of each descriptive answer of the set of possible descriptive answers for each theoretical optical condition of a plurality of theoretical optical conditions is stored in one of said one or more memory of said computer, and said one or more processor of said computer is programmed to:

a) collect results of said subjective test, performed by asking the subject to describe his visual performance in each real optical condition of said plurality of real optical conditions by choosing, for each real optical condition, one descriptive answer among said set of possible descriptive answers, said results comprising each descriptive answer chosen and the corresponding real optical condition, and b) determine the value of said magnitude by taking into account said initial model and each descriptive answer collected.

2. The system according to claim 1, wherein, in b), said computer is programmed to compare said initial model and at least one descriptive answer collected, and determine said value of said magnitude based on this comparison.

3. The system according to claim 2, wherein said initial model comprises an initial model curve and said computer is programmed to perform, in b), the following:

plotting at least one collected descriptive answer chosen by the subject against the corresponding real optical condition, and superposing said initial model curve on the plot thus obtained so that the initial model curve fits the plot, and determining said value of said magnitude taking into account relative positions of said initial model curve and said plot.

4. The system according to claim 1, wherein said initial model comprises an initial model curve and said computer is programmed to perform, in b), the following:

plotting at least one collected descriptive answer chosen by the subject against the corresponding real optical condition, and superposing said initial model curve on the plot thus obtained so that the initial model curve fits the plot, and determining said value of said magnitude taking into account relative positions of said initial model curve and said plot.

5. The system according to claim 1, wherein said initial model comprises an initial set of data and said computer is programmed to perform, in b), the following:

processing statistically said initial set of data and said collected descriptive answer, and determining said value of said magnitude taking into account this statistical process.

6. The system according to claim 1, wherein said computer is programmed to perform, in b), the following:

modify said initial model to obtain a modified model taking into account each descriptive answer of the subject and the corresponding real optical conditions, and compare said modified model and each descriptive answer collected and determine said value of said magnitude based on this comparison.

7. The system according to claim 6, wherein said modified model comprises a modified model curve and said computer is programmed to perform, in b), the following:

plotting each collected descriptive answer chosen by the subject against the corresponding real optical condition, and superposing said modified model curve on the plot thus obtained so that the modified model curve fits the plot, and determining said value of said magnitude taking into account relative positions of said modified model curve and said plot.

8. The system according to claim 7, wherein said modified model comprises a modified set of data and said computer is programmed to perform, in b), the following:

processing statistically said modified set of data and said collected descriptive answer, and determining said value of said magnitude taking into account this statistical process.

9. The system according to claim 6, wherein said modified model comprises a modified set of data and said computer is programmed to perform, in b), the following:

processing statistically said modified set of data and said collected descriptive answer, and determining said value of said magnitude taking into account this statistical process.

10. The system according to claim 1, wherein said initial and/or modified model takes into account one or more personal features of said subject, said personal feature including at least a value of:

a social parameter including age, gender, geographical origin, eyecare history, a morphological parameter including pupil size, interpupillary distance, an optical parameter including ametropia type and/or value, astigmatism, eye-lens distance, a set-up parameter including starting point of the subjective test, type of stimulus, distances for testing far vision or near vision, distance between phoropter and eye, a visual parameter including acuity, previous answers to subjective test, eye dominance, binocular vision, ocular motility, and a behavioral parameter including rapidity of previous answers to subjective test, sensitivity to a variation of at least an optical feature of at least an ophthalmic lens.

11. The system according to claim 1, wherein said set of possible descriptive answers comprises the following answers:

better visual performance with first real optical conditions, better visual performance with second real optical conditions, and no difference perceived between first and second real optical conditions.

12. The system according to claim 1, wherein said initial model is determined statistically based on a reference set of data previously collected while performing said subjective test on a plurality of reference subjects, said reference set of data comprising:

personal features of each reference subject, and real optical conditions and corresponding answers of each reference subjects, and said personal feature including at least a value of:

a social parameter including age, gender, geographical origin, eyecare history, a morphological parameter including pupil size, interpupillary distance, an optical parameter including ametropia type and/or value, astigmatism, eye-lens distance, a set-up parameter including starting point of the subjective test, type of stimulus, distances for testing far vision or near vision, distance between phoropter and eye, a visual parameter including acuity, previous answers to subjective test, eye dominance, binocular vision, ocular motility, and a behavioral parameter including rapidity of previous answers to subjective test, sensitivity to a variation of at least an optical feature of at least an ophthalmic lens.

13. The system according to claim 12, wherein said initial model is determined based on average values or weighted average values of a part of the reference set of data selected based on one or more personal feature of the reference subject and/or said initial model is determined using machine learning algorithms and/or neural networks algorithms.

14. The system according to claim 13, wherein, said plurality of reference subjects is selected from a group of reference subjects as having one or more personal features identical or similar to the corresponding personal features of the subject.

15. The system according to claim 12, wherein, said plurality of reference subjects is selected from a group of reference subjects as having one or more personal features identical or similar to the corresponding personal features of the subject.

16. The system according to claim 1, wherein, said computer is programmed to determine said value of said magnitude based on a position of the initial or modified model curve relative to a plot when the position is determined after a predetermined number of trials or when the position is not modified between two successive trials of the subjective test by more than a predetermined amount.

17. The system according to claim 1, wherein said computer is programmed to compare each of the collected descriptive answers corresponding to real optical conditions to said initial or modified model and, when this comparison shows that difference between a specific collected descriptive answer corresponding to specific real optical conditions and the initial, respectively modified, model is over a predetermined threshold, this specific collected descriptive answer is identified as inconsistent, and, optionally, when a number of inconsistent answers is over a predetermined threshold, the initial or modified model is modified to reduce the number of inconsistent answers.

18. A method for determining a value of a magnitude associated with a subjective value of an optical feature of a corrective lens adapted to an eye of a subject, said optical feature being applicable to compensate for compensate a visual defect of the subject, through a subjective test where the subject is asked to describe his visual performance in a plurality of real optical conditions by choosing one descriptive answer among a set of possible descriptive answers, each real optical condition of said plurality of real optical conditions comprising a value of an other optical feature of an optical component placed in front of the eye of the subject, the method comprising:

providing an initial model giving a probability of each descriptive answer of the set of possible descriptive answers for each theoretical optical condition of a plurality of theoretical optical conditions;

performing said subjective test by asking the subject to describe his visual performance in each real optical condition of said plurality of real optical conditions by choosing, for each real optical condition, one descriptive answer among said set of possible descriptive answers;

collecting each descriptive answer of the subject and the corresponding real optical condition; and determining the value of said magnitude by taking into account said initial model and each descriptive answer collected.

* * * * *